(12) United States Patent
Fugal

(10) Patent No.: US 8,634,074 B2
(45) Date of Patent: Jan. 21, 2014

(54) METHOD AND SYSTEM FOR HIGH VOLUME SAMPLE RATE HOLOGRAPHIC PARTICLE MEASUREMENT

(75) Inventor: Jacob Fugal, Mainz (DE)

(73) Assignee: University Corporation for Atmospheric Research, Boulder, CO (US)

( * ) Notice: Subject to any disclaimer, the term of this patent is extended or adjusted under 35 U.S.C. 154(b) by 287 days.

(21) Appl. No.: 13/087,503

(22) Filed: Apr. 15, 2011

(65) Prior Publication Data

US 2011/0299079 A1 Dec. 8, 2011

Related U.S. Application Data

(60) Provisional application No. 61/352,491, filed on Jun. 8, 2010.

(51) Int. Cl.
*G01N 15/02* (2006.01)

(52) U.S. Cl.
USPC .............................................. 356/336; 356/28

(58) Field of Classification Search
USPC .......................................... 356/335–343, 28
See application file for complete search history.

(56) References Cited

U.S. PATENT DOCUMENTS

| | | | | |
|---|---|---|---|---|
| 3,520,610 A | * | 7/1970 | Parrent, Jr. et al. | 356/71 |
| 7,772,579 B2 | * | 8/2010 | Herzog et al. | 250/574 |
| 7,847,923 B2 | * | 12/2010 | Pittaro et al. | 356/28 |
| 2002/0167672 A1 | * | 11/2002 | Anezaki et al. | 356/458 |
| 2004/0023310 A1 | * | 2/2004 | Kariv et al. | 435/7.2 |
| 2006/0175561 A1 | * | 8/2006 | Estevadeordal et al. | 250/573 |
| 2008/0221812 A1 | * | 9/2008 | Pittaro et al. | 702/66 |

* cited by examiner

*Primary Examiner* — Hoa Pham
(74) *Attorney, Agent, or Firm* — Marsh Fischmann & Breyfogle LLP

(57) ABSTRACT

Methods and systems for measuring particles within a flow are provided. An aircraft transports a high volume sample rate holographic measurement instrument through a particle-containing volume of interest along a reference axis X (time). As the instrument moves relative to the volume of interest, the holographic measurement instrument transmits a collimated light beam across the volume of interest along an optical axis Z. The light beam interacts with particles contained within the volume of interest, and a high-speed, one-dimensional detector array detects incident light reflecting patterns of light intensity levels that are associated with the interaction between the light beam and the particles. A processor integrates information relating to the detected patterns and a rate of relative movement between the measurement probe and the volume of interest to determine at least a statistically meaningful sampling of time-dependent particle distribution information associated with an entirety of the volume of interest. Using the time-dependent particle distribution information and automatic reconstruction algorithms running on the processor, the processor reconstructs holograms that depict the particles within the volume of interest. These holograms are then used to measure a spatial distribution, size distribution, number density or concentration, and/or shape of the particles within the volume of interest.

25 Claims, 9 Drawing Sheets

US 8,634,074 B2

METHOD AND SYSTEM FOR HIGH VOLUME SAMPLE RATE HOLOGRAPHIC PARTICLE MEASUREMENT

CROSS REFERENCE

This application claims the benefit, under 35 U.S.C. §119(e), of the filing date of U.S. Provisional Application No. 61/352,491 entitled "METHOD AND SYSTEM FOR HIGH VOLUME SAMPLE RATE HOLOGRAPHIC PARTICLE MEASUREMENT," having a filing the of Jun. 8, 2010, the entire contents of which are incorporated by reference herein as if set forth in full.

FIELD OF THE INVENTION

This invention relates to particle measurement in general and more particularly to a holographic system for measuring size distributions, spatial distributions, and number densities of cloud particles.

BACKGROUND OF THE INVENTION

It is often desirable to understand accurate size distributions, spatial distributions, and number densities of particles within a flow, and more specifically, of cloud particles. For example, scientists continually seek a better understanding of how local cloud particle size distributions vary inside cloud regions by cloud age and type, how cloud particles are spatially distributed on sub-centimeter scales due to mixing, entrainment, and turbulent processes, and how ice and liquid water particles are spatially distributed or partitioned within mixed-phase regions of a cloud. This type of information is useful in understanding and modeling cloud processes such as precipitation formation and radiative transfer and for validation of remote sensing and satellite measurements.

Many methods and instruments have been devised to measure cloud particles, yet there remains considerable uncertainty in measuring small particles between approximately 10 µm and 100-200 µm using standard in-situ imaging instrumentation (e.g., aircraft imaging probes). Imaging instrumentation images particles appearing at the focus of a laser sheet by using a linear photodiode array to detect intensity levels of light impinging on the linear array (e.g. light that has been scattered by the particles or light that has not been absorbed by the particles). Because small particles have a small depth of focus, conventional imaging probes have correspondingly low sample volumes and volume sample rates. That is, there is only a small area of focused light through which particles to be imaged may appear.

Beyond a small depth of focus, there is significant uncertainty in the depth of focus for small particles due to variances in optical alignment and the relative velocity between the instrumentation and the particles to be imaged. This depth of focus uncertainty causes uncertainty in sample volume size, which translates to uncertainty in particle concentrations. This occurs because particles outside the depth of focus of traditional imaging probes appear blurry or fainter and larger in size than the focused imaged particle, resulting in over-estimation of particle sizes. Further, out-of-focus particles can appear fragmented which leads to miscounting and under-sizing of the real particle population. See Korolev, A.: Reconstruction of the Sizes of Spherical Particles from their Shadow Images, Part I: Theoretical Considerations, J. Atmos. Ocean. Tech., 24, 376-389, 2007.790. The depth of focus issues associated with imaging small particles also lead to particle size uncertainty. Namely, while traditional imaging probes only image particles appearing within the depth of focus of the laser sheet, the exact location of a particle within the depth of focus is unknown. Because any distance between the particle to be imaged and the exact focal point of the laser sheet introduces error into the particle image, there is uncertainty regarding the actual size of imaged particles.

SUMMARY OF THE INVENTION

The present invention relates to a particle measurement system and associated methodologies for the measurement of particles within a volume of interest (e.g., measurement of size distribution, spatial distribution, number density, and/or shape of particles within the volume of interest as well as measurement of velocimetry characteristics or other derivative information). While particles are detailed herein as particles within a cloud volume of interest, the particle measurement system and associated methodologies are applicable to any particle flow analysis in which the particles have a mean velocity that is much higher than variations in the mean velocity and that would benefit from a time-dependent analysis in a second dimension. For instance, the volume of interest may contain any type of particles in a flow, including, for example, biological cells, bubbles, or chemically coated spheres within a flow. In one demonstrative implementation, the particles may include aerosol particles within a cloud volume of interest. Further the particles may include liquid particles having a cohesive spherical shape or ice particles having an isometric, quasi-isometric, or irregular shape that is difficult to estimate without a full particle image.

As discussed above, the inventors have recognized that the in-focus imaging method of particle measurement is deficient in several meaningful ways. In this regard, a holographic measurement method, which does not use focused light in particle measurement, provides for much larger, more certain sample volumes and corresponding volume sample rates. This, in turn, allows for more accurate measurement of particle shapes, sizes, and concentrations within a sample volume. That said, the holographic measurement principal retains certain volume sample rate limitations and is limited to discrete, two-dimensional snapshots of particles within a sample volume. This approach is time-independent and does not account for the velocity of the particles within the flow. Thus, the inventors have recognized a need for a high volume sample rate holographic measurement instrument and reconstruction methodology for providing cumulative information regarding the particles within a volume of interest as a function of time along a flight path of the instrument.

In particular, a first aspect of the present invention includes methodology for in situ particle measurement that provides a high volume sample rate, such as a substantially continuous sampling of a volume of interest. The methodology comprises moving a measurement instrument at a first velocity relative to a reference axis that intersects a volume of interest, where the volume of interest includes a number of particles to be measured, and where the particles are moving at a second velocity relative to the reference axis. As the measurement instrument moves through the volume of interest, a light beam is transmitted across the volume of interest. The light beam may be a laser sheet or beam that interacts with individual particles and may be a collimated or slightly diverging/converging beam. A sensor array of the measurement instrument then detects incident light that reflects patterns associated with an interaction of the light beam with the particles. In addition, one or more computer processors determine, based at least in part on the second velocity, an effective pixel pitch of the array along the reference axis and integrate data collected over time using the array in order to form one or more holograms that provide cumulative information regarding the particles within the volume of interest as a function of time along the reference axis.

One embodiment is capable of reconstructing the holograms using an automated reconstruction algorithm running on the one or more computer processors. The automated algorithm may be based on a Rayleigh-Sommerfeld kernel with a low-pass filter, or it may be any other appropriate reconstruction algorithm. The algorithm may be written in any appropriate coding language, including, for example, the MATLAB language. Further, the reconstructed holograms may be used to measure a size distribution, spatial distribution, number density, and/or shape of the particles within the volume of interest.

In another embodiment, the methodology further includes determining three-dimensional position information for each of the particles within the volume of interest. The three-dimensional position information may include an X-position, a Y-position, and a Z-position for each particle. More specifically, the X-position may be a position along the reference axis in the time dimension, and the Z-position may be a position along an optical axis of the measurement instrument. Determining the X-position may include correlating the data collected over time using the array and the velocity or speed of relative motion between the measurement instrument and the reference axis, which may fluctuate and which may vary along the described optical axis (i.e., the Z-axis).

The sensor may be an array of any appropriate size, type, and/or configuration. In this regard, the array may be arranged in rows of M×N pixels, where M<<N, as appropriate (e.g. 1×100 up to 1×1024). For instance, the array may be a one-dimensional photodiode array having, for example, 128, 256, 1024 pixels or elements. In addition, each pixel may have between 3 bits (8 shades/intensities of gray) and 8 bits (256 shades/intensities of gray), where the higher gray levels may be strategically spaced to best resolve holograms with the least amount of information.

Another aspect of the present invention includes a method of particle measurement that provides at least a statistically meaningful sampling of particle distribution information for a volume of interest. The method includes receiving first input information regarding a rate of relative motion between a measurement instrument and a volume of interest that contains numerous particles to be measured, where the measurement instrument transmits a collimated light beam across the volume of interest. The methodology also includes receiving, from a detector array, second input information relating to incident light reflecting patterns associated with an interaction between the collimated light beam and individual particles. By operating one or more processors, the first and second input information is used to obtain at least a statistically meaningful sampling of time-dependent particle distribution information for the volume of interest. The time-dependent particle distribution information relates to at least one of a spatial distribution of the particles, a size distribution of the particles, a number density of the particles, and a shape of the particles within the volume of interest.

In one embodiment, one or more of the particles may be between 1 μm and 200 μm in diameter. In addition, the statistically meaningful sampling of time-dependent particle distribution information may encompass all of the particles within the entirety of the volume of interest. In another embodiment, the methodology may further include reconstructing one or more time-dependent holograms using the time-dependent particle distribution information. The reconstructing may be accomplished using any appropriate automated reconstruction algorithm running on the processors.

Yet another aspect of the present invention involves a particle measurement system that features a detector array with a response time that allows for substantially continuous sampling of incident light reflecting patterns associated with an interaction of a collimated light beam and illuminated particles within a particle-containing volume. The particle measurement system includes a particle measurement probe mounted for a rate of relative movement between a particle-containing volume and the particle measurement probe. The particle measurement probe includes a light source and a detector array. The light source emits a collimated light beam that illuminates particles within the particle-containing volume, and the detector array senses incident light reflecting patterns associated with an interaction of the light beam with the particles. The array has a response time that allows for substantially continuous sampling. The particle measurement system also includes a processor that integrates data collected over time using the array to form one or more holograms that provide cumulative information regarding the particle-containing volume.

In one embodiment, the data collected over time using the array may represent data encompassing an entirety of the particle-containing volume. Another embodiment may further include one or more analog-to-digital converters to digitize the data collected over time using the array, or to create digitized holographic data. The digitized holographic data may be stored in a memory before it is later transferred to the processor for integration and hologram reconstruction.

In another embodiment, the holograms may allow for measurement of all of the particles within the particle-containing volume. In this regard, the measurement of the particles may relate to at least one of a spatial distribution of the particles, a size distribution of the particles, a number density of the particles, and a shape of the particles within the particle-containing volume. The measurement of the particles may also relate to three-dimensional positions associated with the particles, or more specifically, to an X-position, a Y-position, and a Z-position within the particle-containing volume. The X-position may define a position along an axis that parallels a direction of relative movement between the particle containing volume and the particle measurement probe and may also be a function of time as well as the rate of relative movement. The Z-position may be a depth-position along an optical axis that is defined by the laser beam.

While there is relative motion between the measurement probe and the volume of interest, the probe may be stationary while the particles move relative to the probe. For example, in one embodiment, the measurement probe may be mounted to an aircraft and moved through the volume of interest, while in another embodiment, the measurement probe may be mounted at a fixed position within an air duct. In addition, the rate of relative movement between the particle-containing volume and the measurement probe may fluctuate.

As discussed above, the detector array may have any appropriate number of pixels (e.g., 128, 256, 1024) and each pixel may be, for example, a 3 to 8 bit pixel that senses between 8 and 256 shades of gray. Further, the detector array may be arranged in rows of M×N pixels, where M<<N.

Another aspect of the present invention includes a method of particle measurement that allows for the measurement of a shape of each particle within a volume of interest. The method involves providing a measurement probe for transmitting a collimated light beam across a volume of interest containing numerous particles to be measured, moving the measurement probe relative to the volume of interest, detecting incident light reflecting patterns associated with a diffraction of the collimated light beam by individual particles, and processing data collected over time using the array to provide a shape of each particle within the volume of interest.

In one embodiment, the collimated light beam may be composed of reference waves, and the diffraction of the collimated light beam may result in diffraction waves. In this embodiment, the patterns reflected in the detected incident light are formed by an interference between the reference waves and the diffraction waves. In another embodiment, the processing may include reconstructing one or more holograms that provide cumulative information regarding the particles within the volume of interest. The holograms may then be used to determine a shape or shapes of the particles that are represented in the holograms.

Another aspect of the present invention provides a method for obtaining particle distribution information associated with a volume of interest at a high volume sample rate. The method involves providing a holographic measurement probe for transmitting a collimated light beam across a volume of interest containing numerous particles to be measured, moving the holographic measurement probe relative to the volume of interest, detecting incident light reflecting patterns associated with a diffraction of the collimated light beam by individual particles, and processing data collected over time using the array to provide a shape of each particle within the volume of interest. The sensor array and the processors operate to provide the particle distribution information at a volume sample rate of at least 100 cm$^3$/s. In other embodiments, the sensor array and the one or more processors may operate to provide the particle distribution information at volume sample rates of at least 1,000 cm$^3$/s, 10,000 cm$^3$/s, or even higher.

BRIEF DESCRIPTION OF THE DRAWINGS

For a more complete understanding of the present invention and further advantages thereof, reference is now made to the following Detailed Description taken in conjunction with the accompanying drawings, wherein.

DETAILED DESCRIPTION OF THE INVENTION

The following description describes exemplary embodiments of a system and method of particle measurement. Specifically, the description details an embodiment of in situ measurement of cloud particles using a high volume sample rate holographic measurement instrument (hereinafter "measurement instrument," "instrument," "measurement probe," or "probe") to gather holographic data associated with a particle-containing cloud volume of interest. The holographic data may then be numerically reconstructed to form numerous holograms that provide cumulative information regarding the particles contained within the volume of interest. The following description should be understood as exemplifying the invention without limiting it.

Reliable measurements of both liquid and ice cloud particle size distributions, spatial distributions, number densities, and shapes are integral for understanding and modeling cloud processes, including precipitation formation and radiative transfer. Accurate measurements of the sizes, shapes, and concentrations of liquid and ice particles within cloud formations are also useful for validation of remote sensing and satellite measurements. In this regard, airborne particle measurement instruments are useful tools for atmospheric researchers because they are capable of imaging cloud particles within a cloud volume of interest. These images are, in turn, extremely valuable in determining the nature and behavior of particles within the cloud volume of interest.

Figure 1:
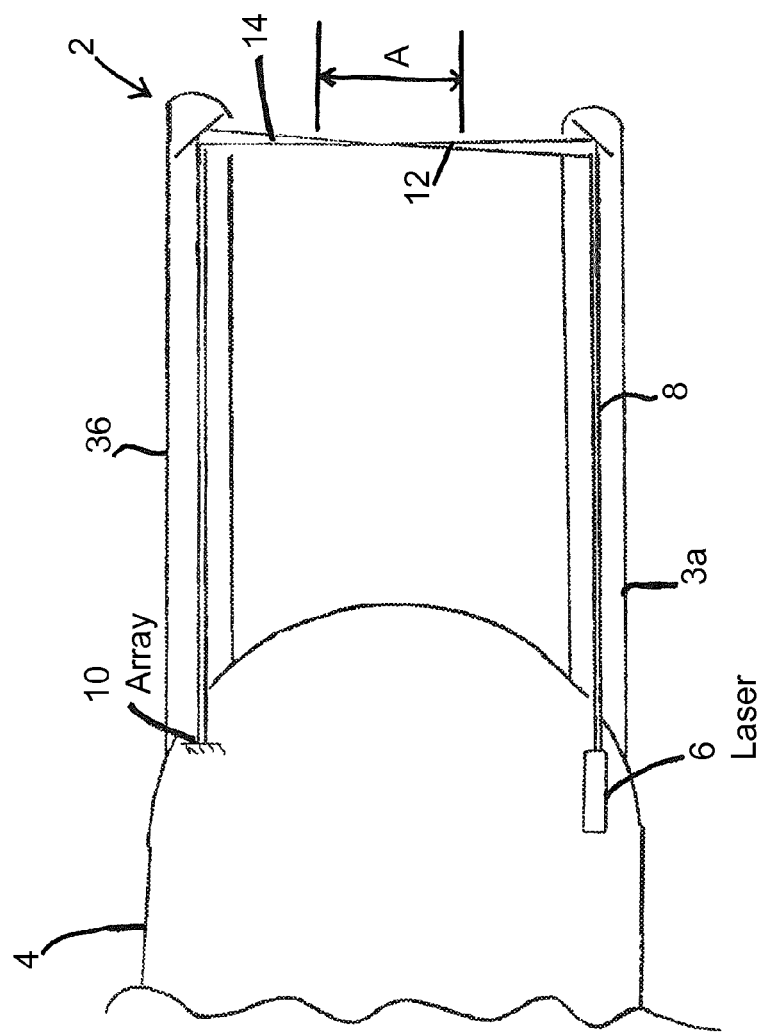
FIG. 1 illustrates an imaging-style measurement instrument as mounted to a base of an aircraft.

Unfortunately, many current measurement instruments are imaging-style instruments that exhibit several disadvantages. Imaging-style probes image particles that appear at a focus (i.e., within a depth of focus) of a laser beam or sheet by detecting, on a linear detector array (e.g., a photodiode array), intensity levels of leftover light not absorbed by the illuminated particles. To illustrate, FIG. 1 shows an imaging-style measurement probe 2 as mounted to a base of an aircraft 4. The probe 2 has two arms 3$a$-$b$. A laser 6 transmits a light sheet (i.e., a laser beam that is elongated in one direction and not in another) 8 through the arm 3$a$, across a particle-containing volume, and through the arm 3$b$ to a detector array 10. Within the particle-containing volume of interest, the light sheet 8 is focused. A depth of focus A represents a measurement of a depth of acceptable sharpness within the object space. That is, a particle 12 falling within the depth of focus A would appear on the array 10 and result in a focused image, while a particle 14 falling outside the depth of focus A would either not appear on the array 10 or the resulting image would be unfocused.

With in-focus imaging, the depth of focus is a function of particle size and is found by, $$DOF \sim 3/2 D^2 \lambda,$$

where D is the particle diameter and $\lambda$ is the wavelength of the light sheet or beam. The depth of focus is highly sensitive to particle diameter, and for small particles having diameters between ~10 μm and ~200 μm, the depth of focus is very narrow and results in a small, particle-size-dependent sample volume. Because the size of the sample volume is particle-size-dependent, the volume sample rate is also particle-size-dependent. Moreover, imaging particles that fall outside the depth of focus can be missed, resulting in large uncertainties in the concentration of smaller particles.

The depth of focus for small particles is also uncertain due to variances in instrumentation resolution and the relative velocity between the instrumentation and the particles to be imaged. This uncertainty contributes to the problem of poorly defined sample volumes and volume sample rates, and therefore, uncertainty in the estimates of particle concentration or number density. There is also greater uncertainty in the particle size distributions from imaging-style probes because out-of-focus particles appear as a diffraction pattern larger than its image, resulting in over-sizing. Such patterns can also appear fragmented, leading to over-counting and under-sizing of the real particle distributions.

Figure 2:
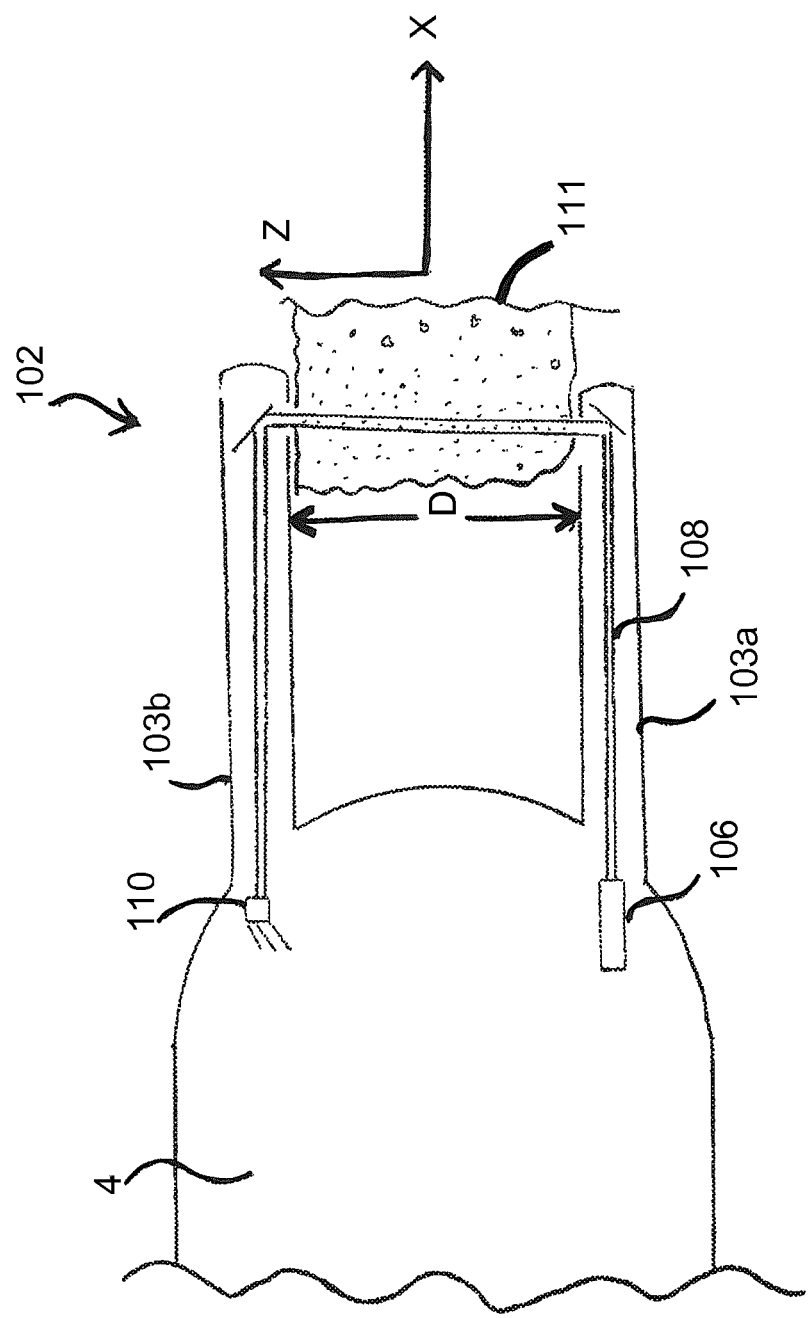
FIG. 2 illustrates an embodiment of airborne holographic measurement instrument as mounted to a base of an aircraft.

Digital in-line holography probes overcome several of these limitations. FIG. 2 illustrates an exemplary holographic measurement instrument 102 as mounted to a base of the aircraft 4. In this embodiment, the holographic instrument 102 includes a laser 106, two arms 103a-b, and a digital camera 110. The laser 106 transmits a light sheet or beam 108 that travels along the arm 103a before it is redirected across a volume of interest 111 containing numerous particles 112 to be measured. Unlike the imaging-style probe 2 of FIG. 1, the light sheet 108 is not focused, and as a result, collimated light (i.e., unfocused light with nearly parallel rays) is transmitted across the volume of interest 111. The collimated light interacts with the particles 112 in its path and scatters, thereby forming diffraction or scattered waves associated with each of the illuminated particles 112. As the holographic instrument 102 moves across the volume of interest 111, the camera 110 records interference patterns associated with the interaction between the light sheet 108 and the particles 112 at defined intervals. Each time the camera 110 records an image, it captures a discrete snapshot of the particles 112 within a single sample volume at a set moment in time, where the larger volume of interest 111 includes numerous sample volumes.

Figure 3:
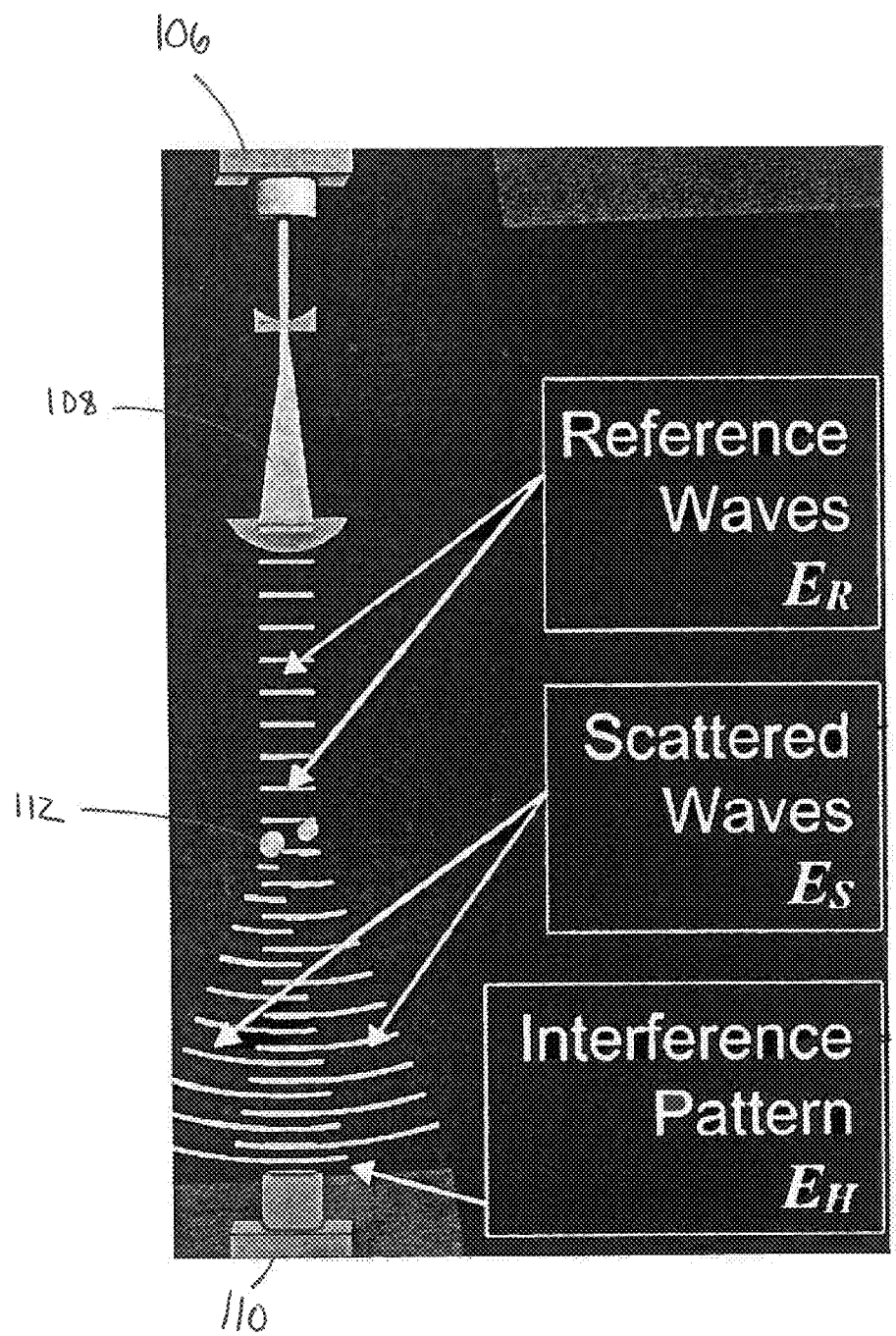
FIG. 3 presents a graphical representation of the holographic measurement principal.

FIG. 3 graphically illustrates the holographic measurement principal. As applied to the holographic measurement instrument 102, discussed above, an in-line hologram is an interference pattern resulting from the superposition of reference waves $E_R$ of the light sheet or beam 108 and diffraction or scattered waves $E_S$ that are formed through the interaction between the light sheet or beam 108 and the illuminated particles 112 within the sample volume. Conceptually, the resulting holographic electric field $E_H$ at the measurement plane of the camera 110 is $E_H=E_R+E_S$. Two-dimensional holograms that depict the particles 112 may then be numerically reconstructed using digitized data that reflects the holographic electric field $E_H$, as the detector measures the modulus squared of $E_H$, or the intensity of the hologram.

Because the holographic measurement principal does not image particles that appear at a focus of the laser sheet or beam, the in-line holographic measurement instrument 102 may accurately reconstruct particles across a much larger, and more constant, depth D between the arms 103a and 103b of FIG. 2. As a result, the sample volume size and uncertainty limitations arising from the particle-size-dependent depth of focus, discussed above in relation to the imaging-style instrument 2 of FIG. 1, are less applicable. Indeed, the holographic probe 102 provides a well-defined sample volume that is extended over the imaging measurement principal by approximately two orders of magnitude.

Because there is certainty in the volume sample size, there also is greater certainty in the volume sample rate as well as the particle concentration or number density within each sample volume. Further, as discussed below, the holographic probe 102 has the advantage of being able to focus the particle even if diffracted to achieve a more accurate size. Moreover, a position for each of the particles 12 along the optical axis may be calculated with greater certainty, whereas imaging-style probes cannot calculate this depth dimension.

While the benefits of digital in-line holography instruments are significant, such instruments record snapshots taken on an M×N aspect ratio of, for example, 4:3 or 3:2, resulting in a series of discrete two-dimensional holograms (i.e., snapshots of independent sample volumes) along the flight path. In this regard, the two-dimensional snapshots are reconstructed in a time-independent manner and without accounting for the velocity of the particles.

In addition to recording discrete snapshots of sample volumes within the volume of interest, existing holography instruments often experience a significant time delay between each snapshot. To demonstrate this limitation, we look to a prototype airborne digital holographic instrument, the Holographic Detector for Clouds ("HOLODEC"), discussed in Fugal, J. P., and Shaw R. A.: Cloud Particle Size Distributions measured with an Airborne Digital In-line Holographic Instrument, Atmos. Meas. Tech., 2, 259-271, 2009, which is incorporated in full herein by reference. The HOLODEC measurement instrument employs a 527 nm wavelength pulsed laser having a pulse width of 20 ns and a 1020×768, 4.65 µm pixel, 8-bit grayscale camera. The sample volume is determined by a sensor area of the camera that is unaffected by noise from edge effects as well as the space between the arms of the probe that is not severely affected by airstream distortion or the boundary layer around the instrument housing, resulting in a valid, discrete sample volume of 4.3×3.6×25 mm$^3$ or approximately 0.39 cm$^3$. With a flight speed of 100 m/s, the HOLODEC measurement instrument records one approximate sample volume every 7 meters or 0.07 seconds for an approximate volume sample rate of 5.5 cm$^3$/s.

Figure 4:
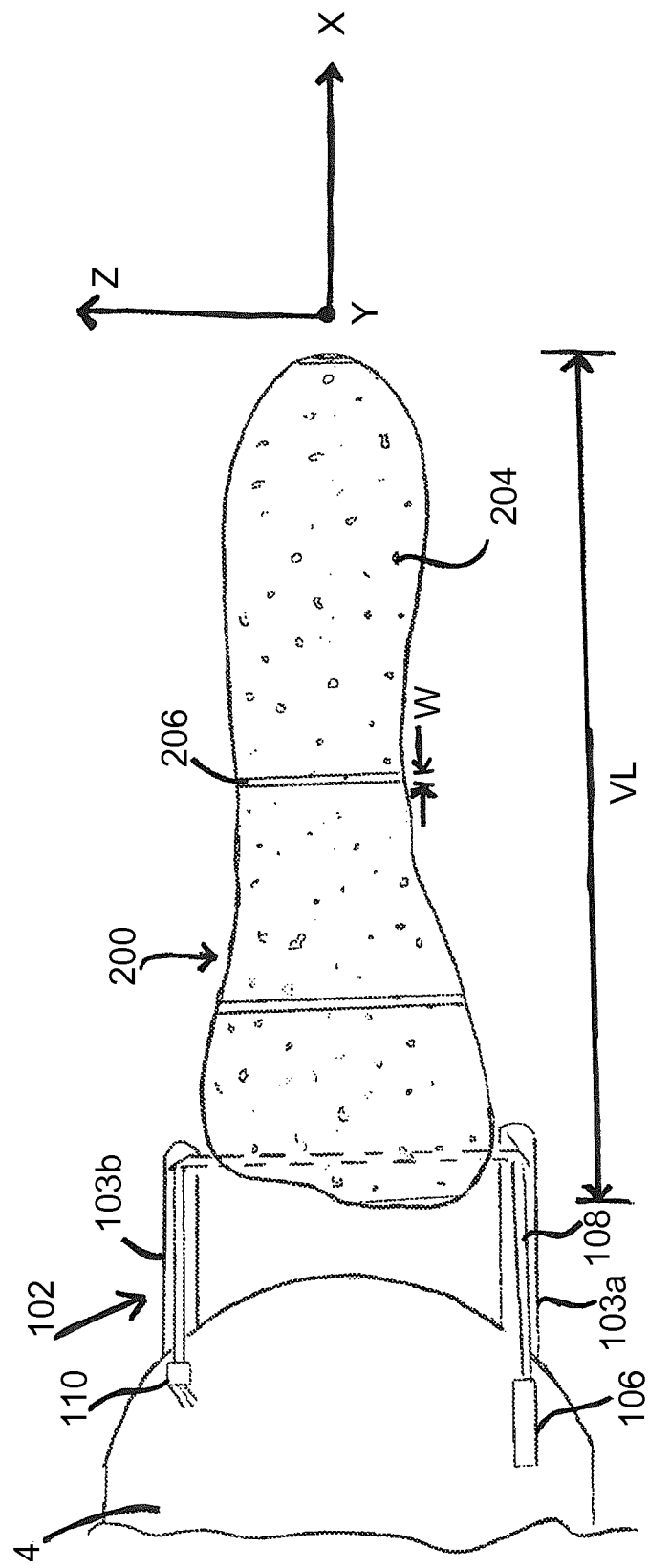
FIG. 4 illustrates a top sectional view of an exemplary cloud volume of interest and one embodiment of a holographic measurement instrument.

FIG. 4 illustrates a top sectional view of the holographic measurement instrument 102 as is moves across an exemplary cloud volume of interest 200 along a reference axis X. In this example, the holographic measurement instrument 102 is the HOLODEC measurement instrument discussed above. Reference axes X, Y, and Z bisect the volume of interest 200 at perpendicular angles, where the reference axis X parallels a direction of movement of the holographic measurement instrument 102 relative to the volume of interest 200 (i.e., the flight path) and the reference axis Z is the optical axis. In one example, the volume of interest 200 has a length VL of 28 meters and includes a number of particles 204 to be measured. The particles 204 may be liquid particles of a general spherical shape, ice particles having an isometric, quasi-isometric, or irregular shape, or a mixture of several shapes.

Applying the instrument parameters of the HOLODEC measurement instrument outlined above, and when flown at a velocity of 100 m/s, the measurement instrument 102 may record one 0.4 cm$^3$ sample volume every 7 meters. Thus, the holographic measurement instrument 102 records only four discrete sample volumes 206 within the 28 meter length L of the volume of interest 200, where each of the discrete sample volumes 206 has a width W that corresponds to a width of the laser beam or sheet 108. As a result, and as shown in FIG. 4, a majority of the particles 204 within the volume of interest 200 are not recorded, while other particles 204 are only partially recorded. Thus, while the holographic nature of the measurement instrument 102 allows for a precise two-dimensional measurement in the Y and Z directions, it generally does not allow for a precise three-dimensional measurement of the particles in the X, Y, and Z directions because so many of the particles 204 are not recorded as the measurement instrument 102 moves along the reference axis X through the volume of interest 200. The low sampling rate of the camera 110 makes it difficult to extrapolate particle behavior demonstrated within each of the sample volumes 206 to the entire volume of interest 200, which is necessary for accurate velocimetry and particle shape measurements. More particularly, obtaining discrete snapshots of sample volumes that are significantly spaced apart along the length L of the volume of interest 200 does not provide sufficient particle distribution information to effectively analyze the flow characteristics of the particles 206. Nor does it allow for accurate shape measurements of non-spherical ice particles having complex isometric, quasi-isometric, and/or irregular shapes.

Even if a traditional holographic instrument were fitted with a two-dimensional array/camera capable of continuous sampling along a flight path, holographic data would continue to be captured as discrete two-dimensional snapshots on a two-dimensional M×N aspect ratio, where M>N (e.g., 4:3, 3:2). In this regard, the snapshots are taken independent of a time axis along the flight path such that a velocity of the particles is irrelevant. Therefore, development of a high volume sample rate holographic measurement instrument for small particles between ~10 and ~200 μm that continuously analyzes holograms along a time axis that parallels the flight path in the second dimension is a high priority.

The volume sample rate of a measurement instrument depends upon its sample volume size as well as the frame rate or response time of any corresponding camera or detector array. The response time defines the time interval that exists between each recording of a sample volume. Specifically, the volume sample rate ($cm^3$/s) is found by, Volume Sample Rate=Sample Volume($cm^3$)/frame interval(s).

To most dramatically increase the volume sample rate, the sample volume size must increase, while the frame interval decreases. While using the holographic method of measurement described above relieves the sample volume size limitations associated with in-focus imaging, the holographic method of measurement does not decrease or improve the frame interval of the detector array or camera 110.

Figure 5A:
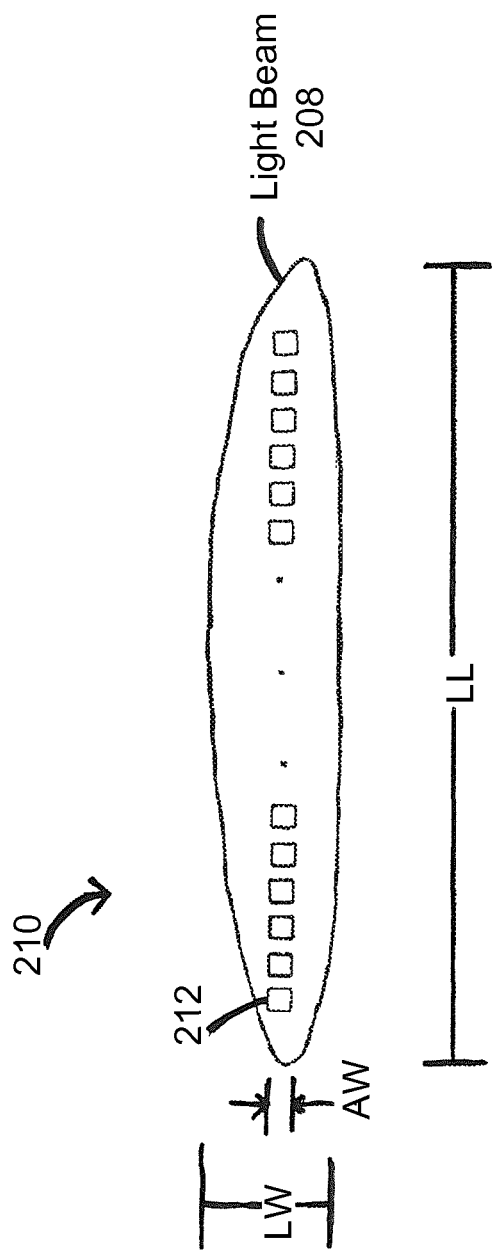
FIG. 5A illustrates one embodiment of a high speed linear photodiode array.
Figure 5B:
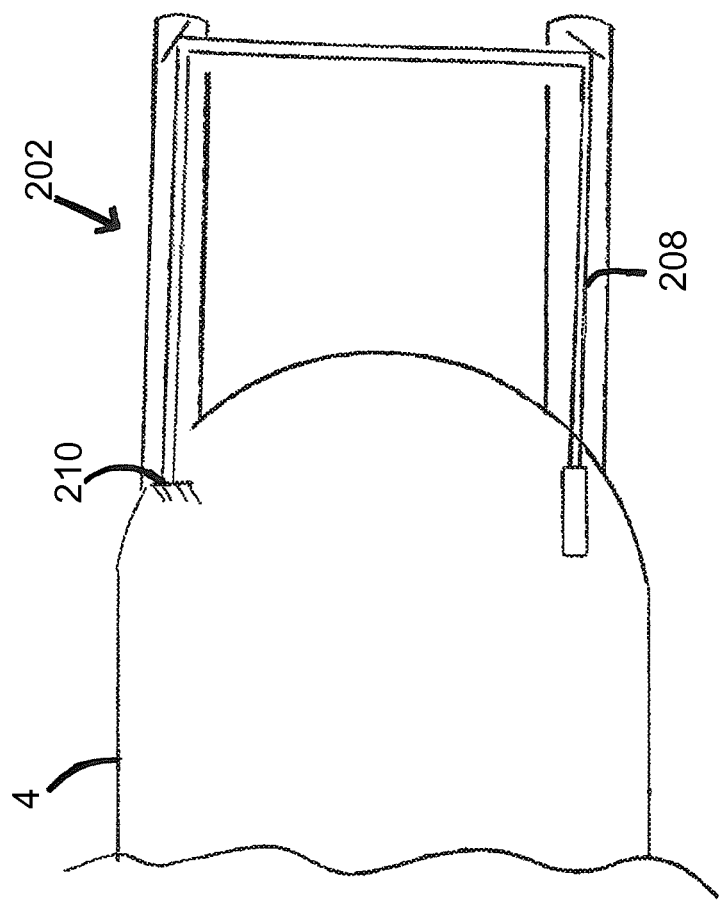
FIG. 5B illustrates one embodiment of a high volume sample rate holographic measurement instrument that incorporates the high speed linear photodiode array of FIG. 5A.

FIG. 5A graphically illustrates one embodiment of a high speed linear photodiode array 210 for use with a high volume sample rate holographic measurement instrument 202, shown in FIG. 5B. In this embodiment, the array 210 may include any appropriate number of pixels or elements (e.g., 128, 256, 1024) 212 of any appropriate size, shape, resolution, and/or configuration. The array 210 may be an M×N array, where M<<N (e.g., M=1, 2, or 3 and N=128, 256, 512, or 1024), to accommodate a width LW of a collimated light sheet or beam 208 and a length LL of the light beam 208 (FIG. 5B). In exemplary implementations, each pixel of the array 210 may have between 3 bits (8 shades/intensities of gray) and 8 bits (256 shades/intensities of gray), and the higher gray levels may be strategically spaced to best resolve holograms with the least amount of information.

Figure 6:
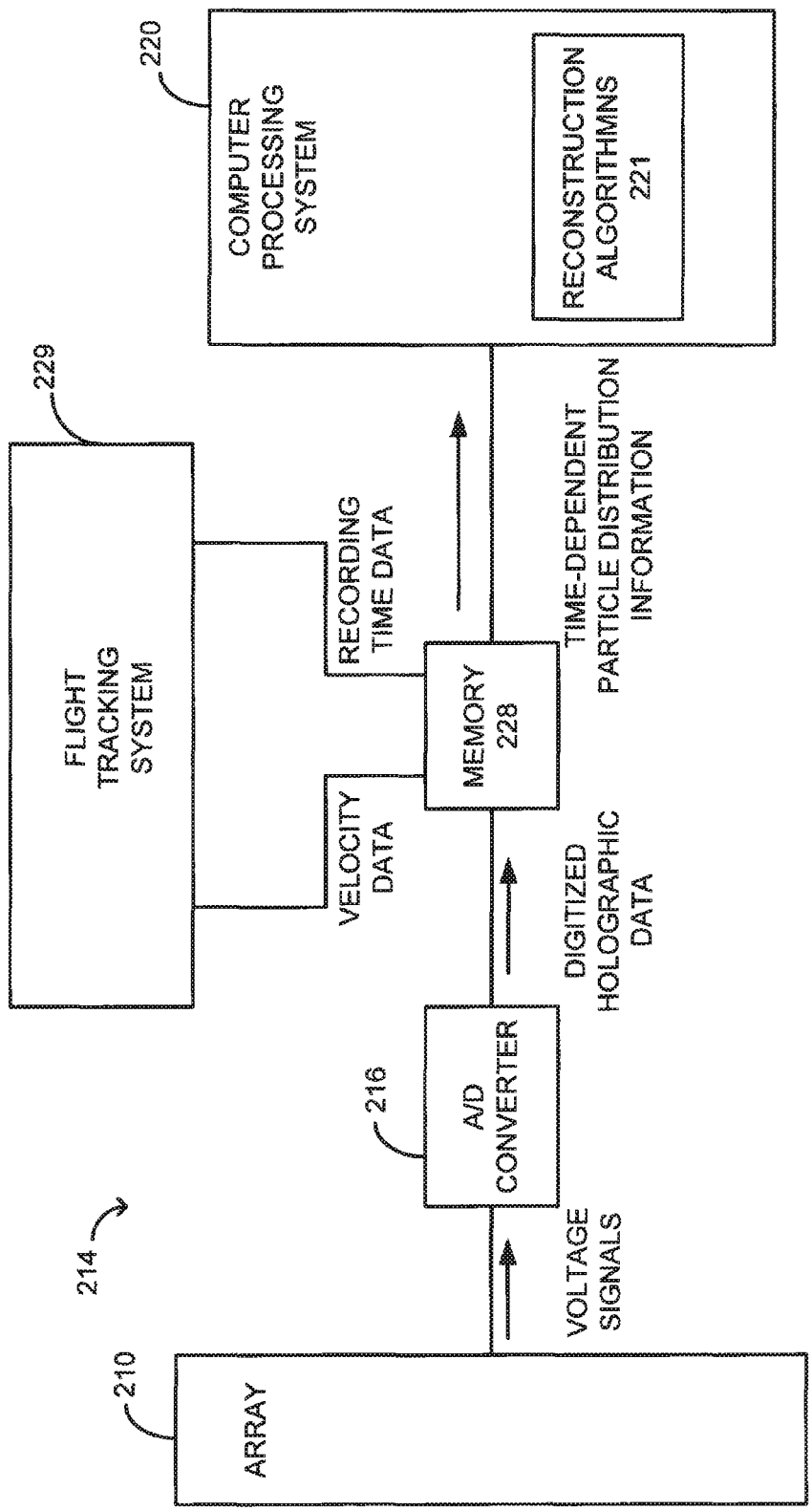
FIG. 6 presents a functional diagram of a data acquisition system for use with the high speed linear photodiode array of FIG. 5A.

FIG. 6 presents a functional diagram of one embodiment of a data acquisition system 214 for the array 210. Employing a 4-bit pixel array, an analog voltage signal reflecting light intensity levels or holographic data (i.e., the holographic energy field EH) for each of the pixels 212 may be digitized using a 4-bit analog to digital ("A/D") converter 216. The 4-bit A/D conversion after the sensor allows for detection of sixteen shades of gray. Notably, the voltage signal for each of the pixels 212 may be routed through a single A/D converter 216 or, in another embodiment, groups of pixels 212 may be muxed through multiple A/D converters 216 to increase system speed. After each voltage signal is digitized, the digitized holographic data may be buffered and organized for meaningful retrieval before being stored within a nonvolatile memory 218. In addition, a flight tracking system 229 may track flight velocity information as well as a flight time associated with each sample volume recorded by the array 210. This information may be stored at the memory 218 along with the digitized holographic data or it may be stored at any other appropriate location.

After data collection is complete (e.g., the data-collection flight is over), the digitized holographic data, the flight velocity information, and the recording time information may be transferred to a computer processing system 220 with adequate processing capability for hologram reconstruction. For example, the computer 220 may be a computer cluster, shared-memory supercomputer, or any other processing system or combination of systems with sufficient computing power. Alternatively, the data may be processed and the holograms reconstructed in real time before the holographic data is deleted.

Figure 7:
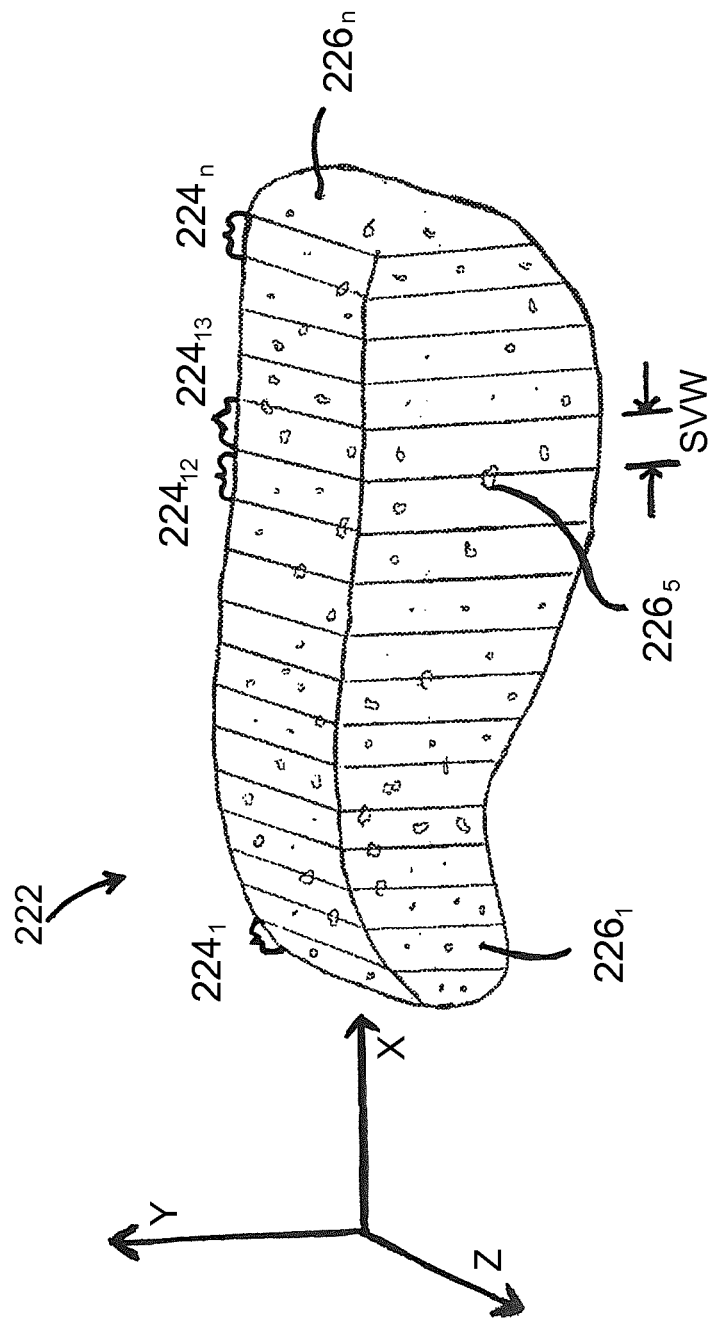
FIG. 7 illustrates a perspective view of an exemplary volume of interest to be measured using the high volume sample rate holographic measurement instrument of FIG. 5B.

In one embodiment, the response time of the array 210 (i.e., the time-lapse between when light intensity levels are detected at each of the pixels 212 and when the corresponding digitized holographic data is stored at the memory 218) is sufficient to record all particles of a volume of interest. Generally described, in relation to the rate of relative movement between the particles and the measurement instrument 202, the response time of the array 210 accommodates a substantially continuous sampling of incident light intensity levels (i.e., the holographic energy fields $E_H$) detected at the pixels 212 of the array 210. Once the digitized holographic data has been gathered, the velocity data and recording time data may be integrated with the digitized holographic data such that when one or more holograms are reconstructed from the digitized holographic data, they provide cumulative information regarding the particles within the volume of interest as a function of time along the X (time) axis that parallels the flight path. For example, FIG. 7 illustrates a perspective view of an exemplary volume of interest 222 to be measured by the holographic measurement instrument 202 using the array 210. The volume of interest 222 is formed of numerous sample volumes $224_{1-n}$ and contains a number of particles $226_{1-n}$ to be measured. In one embodiment, each of the sample volumes $224_{1-n}$ may have a width SVW of 10 μm (a pixel width) that corresponds to the width AW (FIG. 5A) of the array 210. With a relative air-to-particle speed of 200 m/s, the time required for any one of the particles $226_{1-n}$ to move across the sample volume width SVW is ~50 ns. Thus, in this embodiment, to continuously record holographic data (i.e., the holographic electric field $E_H$) associated with each of the particles $226_{1-n}$ within the volume of interest 222 as the measurement instrument 202 moves across the volume of interest 222 along the time X (time) axis, the frame interval for the array 210 is approximately 50 ns, or a 20 MHz line rate. That is, with a 20 MHz line rate, the array 210 will continuously record holographic data associated with an interaction of the reference waves $E_R$ and the diffraction or scattered waves $E_S$ (FIG. 3) for each of the particles $226_{1-n}$ within the volume of interest 222 as the measurement instrument 202 moves across the volume of interest 222 along the X axis (the time axis).

In an embodiment having a 50 ns frame interval (20 MHz line rate), the array 210 of the high volume sample rate holographic measurement instrument 202 may be a 1×128 diode sensor. Each pixel may be 10 μm wide (along the flight direction, or the X axis) and 10 μm tall (along the Y axis), resulting in a 1.28 mm tall sample volume. For 20 μm particles, this embodiment may have a 3.24 cm deep sample volume. With an air speed of 200 m/s, the holographic measurement instrument 202 would have a theoretical volume sample rate that is much higher than the holographic measurement instrument 102 and that is calculated by, Volume Sample Rate=Sample Volume($cm^3$)/Frame Interval(s)=(0.128 cm*0.0010 cm*3.24 cm)/0.00000005 s=8.294 $cm^3$/s~8.3 L/s.

With this volume sample rate, the holographic measurement instrument 202 may measure every particle within the volume of interest 222. If the holographic data recorded for any particular sample volume $224_{1-n}$ reflects only a portion of one or more of the particles $226_{1-n}$, the holographic data recorded for the next sample volume $224_{1-n}$ will include holographic data associated with a remainder of those particles $226_{1-n}$. For instance, FIG. 7 shows that a particle $226_5$ spans two sample volumes $224_{12}$ and $224_{13}$. In this case, a first half of the particle $226_5$ would be reflected in a hologram reconstructed for the sample volume $224_{12}$, while the remainder of the particle $226_5$ would be reflected in a hologram reconstructed for the sample volume $224_{13}$.

In some circumstances, a bottleneck may exist in the passing of holographic data either to computation or to permanent storage. In one embodiment, the data may be written to volatile storage (e.g., random access memory (RAM)) in real-time before data acquisition is paused while the data in volatile storage is written to permanent storage (e.g., a solid-state drive (SSD)). In other embodiments, the data may be directly written to a redundant array of independent disks (RAID) as the data is recorded. Using the example above, the array 210 may collect holographic data at a rate of 1.28 GB/s. This data may reasonably be written across of RAID including seven 480 GB SSDs, each writing at 200 MB/s.

In another embodiment, the array 210 may have a response time that is sufficient to provide a statistically meaningful sampling of holographic data, or a sampling that is statistically representative of the volume of interest 222 such that the holographic data may be extrapolated to the entirety of the volume of interest 222. In this example, combining or integrating the sampling of digitized holographic data saved to the memory 218 with the velocity information as well as the recording time information provides a meaningful statistical sampling of time-dependent particle distribution information that can be extrapolated along the X axis to the entirety of the volume of interest 222. Thus, while in this embodiment, the response time of the array 210 may not record continuously, as discussed above, it may allow for sample volumes to be recorded in a manner that is sufficiently rapid to provide holographic data that statistically represents, and therefore may be extrapolated to, the entire cloud volume of interest 222. For example, the array 210 may have a response time that is sufficient to provide 80 percent volume coverage, 50 percent volume coverage, 10 percent volume coverage, or any other appropriate percentage that allows the holographic data to be meaningfully extrapolated to the entire cloud volume of interest 222.

The combination of the holographic method of measurement along with the high-speed photodiode array 210 and the rapid data acquisition system 214 discussed above allows the digitized holographic data collected by the data acquisition system 214 to be combined with flight velocity information, particle velocity information, and corresponding recording time information to calculate the effective pixel pitch of the M×N array 210 (where M<<N) along the X (time) axis and ultimately obtain time-dependent particle distribution information representing the entire volume of interest 222. Using the time-dependent particle distribution information (Y-position, Z-position, and time along the X axis), one or more automated hologram reconstruction algorithms 221 running on the computer processing system 220 may be implemented to numerically reconstruct holograms that reflect three-dimensional particle position information (X-position, Y-position, and Z-position) for the entire volume of interest 222. The holograms may, in turn, be used to measure the spatial distribution of the particles $226_{1-n}$, the size distribution of the particles $226_{1-n}$, the concentration or number density of the particles $226_{1-n}$, and/or the shape of the particles $226_{1-n}$ as distributed throughout the entire volume of interest 222. Indeed, the success to which holography may be used to make these measurements is dependent upon the ability to accurately reconstruct holograms.

The process of numerical reconstruction of holograms has several key steps. First, the X (time) axis is divided into small sections, and an estimate of the velocity of the particles is used to determine the effective pixel pitch of the M×N array (where M<<N) as it moves within the X (time) axis dimension. This calculation of the pixel pitch affects noise removal and hologram reconstruction, both discussed below, as well as adaptations and/or refinements of the holograms after reconstruction.

Because digitally recorded holograms suffer from multiple sources of noise (e.g., interference fringes from multiple reflections off of optical surfaces, from particles or contaminants stuck to the optics, nonuniformities in the laser field), it is beneficial to implement pre-processing steps that remove as much noise as possible from the data without compromising it. In one embodiment, noise may be removed through a background division method, or by taking the pixel-by-pixel median of several sequential holograms (using the effective pixel pitch) taken before and after the hologram to be reconstructed and dividing the median hologram into the hologram to be reconstructed. The pixel-by-pixel median of the sequential holograms yields a background image nearly free of particles of interest, which change position from hologram to hologram, but retains stationary fringes that persist from hologram to hologram (e.g., noise). As a result, the division eliminates the background noise from the hologram to be reconstructed.

Once noise has been removed, holograms may be reconstructed from the time-dependent particle distribution information using, in one example, an automated reconstruction algorithm employing the filtering form of the Rayleigh-Sommerfeld, or Huygens-Fresnel, kernel with a low-pass filter. This reconstruction method is detailed in Fugal, J. P., Schulz T. J., and Shaw R. A.: Practical Method for Automated Reconstruction and Characterization of Particles in Digital in-line Holograms, Meas. Sci. Technol., 20, 075501, 2009, which is incorporated in full herein by reference.

Notably, even a small amount of error in the particle velocity information impacts the effective pixel pitch calculation. For example, a 5% particle-velocity error results in a 5% error in the effective pixel pitch, which makes it impossible to reconstruct small particles (e.g., up to 20 μm). Because the small particles will only reconstruct when the pixel pitch is accurate, the reconstruction algorithm may vary the effective pixel pitch over a reasonable range, noting the pixel pitch at which the particles may be reconstructed and essentially "backing out" the correct pixel pitch. Then, the velocity of the particles in the flow may be inferred from the known effective pixel pitch. The particle velocities and sizes may be used to remove distortion that the instrument is known to add to the natural position of the particles, yielding more accurate measurements. This distortion-through-velocity information is unreachable in traditional imaging and/or holographic instruments that capture discrete snapshots of particles in a manner that is independent of the particles' velocity along the X (time) axis.

If the laser beam is slightly converging or diverging, as opposed to perfectly collimated, the reconstruction algorithm may also translate a particle's apparent position (which assumes a perfectly collimated beam) to an actual position that accounts for the converging/diverging beam, based on Joseph W. Goodman: Introduction to Fourier Optics, Roberts & Company Publishers, 2005. In addition, the shape of the laser beam (e.g., a 1×M oval beam, a circular beam) may have important measurement consequences that are accounted for in the reconstruction algorithm.

In addition, when measuring size distributions and number densities or concentrations of particles, it is desirable to have a sample volume that is independent of particle size, or in other words, to have particle reconstructions appear the same independent of their depth position along the optical axis Z (FIGS. 4 and 7) inside the sample volume. This is not a problem for particles larger than the diffraction limit at the furthest reconstruction distance in the sample volume, but particles smaller that the diffraction limit appear more visible nearer the detector array. Thus, the low-pass filter calculated for the furthest distance in the sample volume may be applied to enforce the maximum diffraction-limited resolution across all distances in the sample volume, making all particles appear the same throughout the sample volume and allowing all particles to be detected with the same probability throughout the sample volume, as discussed in Fugal, Schultz, and Shaw (2009). The depth positions of particles along the optical axis Z may be determined according to an edge-sharpness algorithm, as discussed in Fugal, Schultz, and Shaw (2009), while particle positions along the flight path axis X may be determined by integrating the holographic data with the data reflecting the time of each recording as well as the corresponding flight velocity.

The automatic algorithms for reconstructing holograms containing large and small particles and finding positions along the flight axis X and the optical axis Z in order to obtain particle size distributions and number densities may be implemented using any appropriate computer code (e.g., MATLAB) on any appropriate computer processing system, such as a computer cluster, supercomputer, or graphical processing unit ("GPU") configured for automated processing of holograms, as discussed above.

Figure 8:
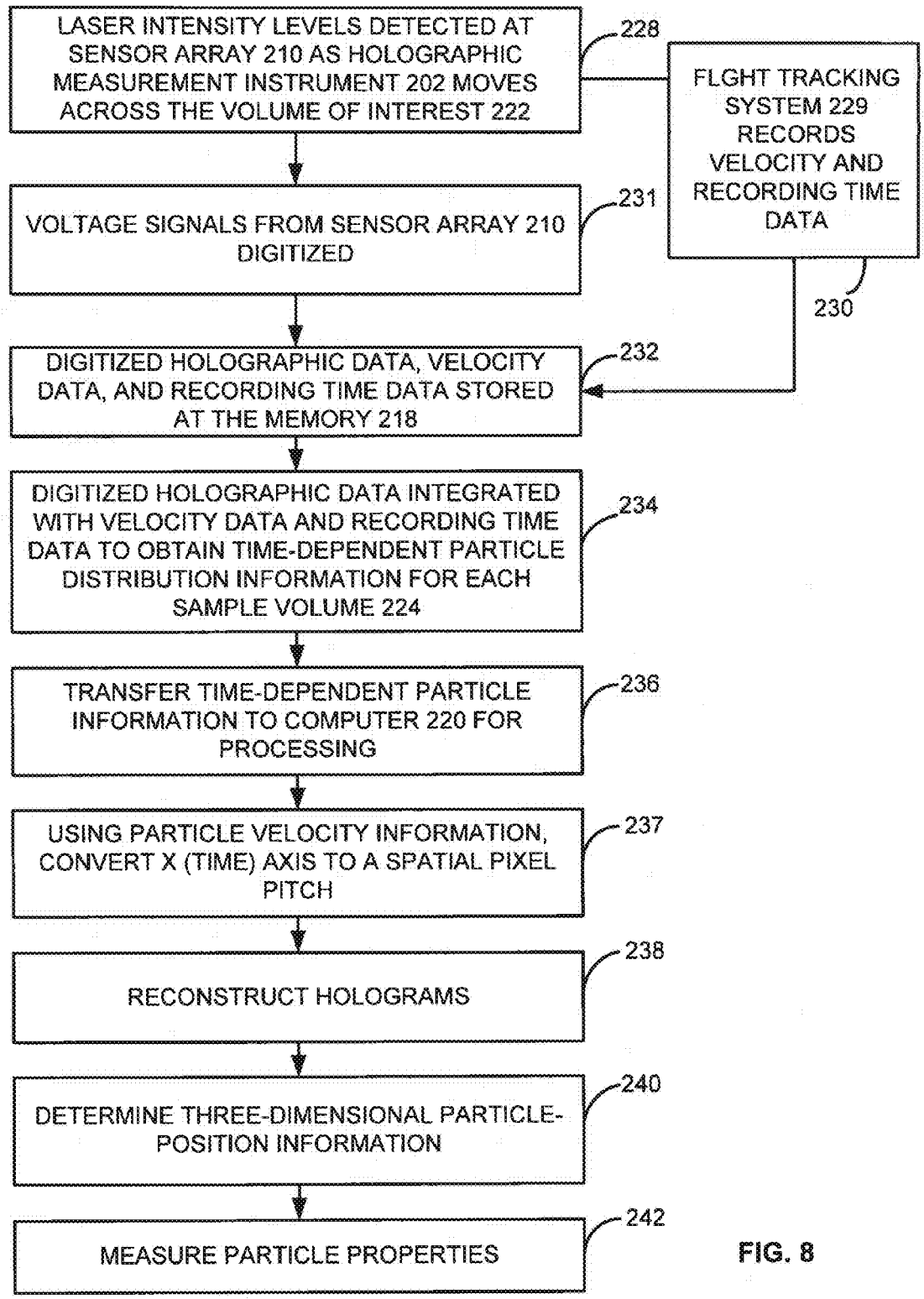
FIG. 8 illustrates a flow chart detailing one embodiment of a method for holographic particle measurement.

FIG. 8 presents a flow chart detailing one embodiment of a method for holographic particle measurement. The method employs the holographic measurement instrument 202 including the high-speed photodiode array 210 and the data acquisition system 214, discussed above. First, the photodiode array 210 produces voltage signals in response to laser intensity levels that are detected at the pixels 212 of the sensor array 210 as the holographic measurement instrument 202 moves across the cloud volume of interest 222 (step 228). At or around the same time, the flight tracking system 229 tracks the flight velocity as well as a time or times at which voltage signals are recorded from the array 210 (step 230). The response time of the sensor array 210, and thus the intervals at which light intensity levels are recorded, may be substantially continuous such that the array 210 records all of the particles $226_{1-n}$ within the volume of interest 222 as the measurement instrument 202 travels across the volume of interest 222. Alternatively, the response time may be sufficiently rapid to obtain statistically meaningful holographic data for later extrapolation to the entire volume of interest 222.

Voltage signals reflecting the detected light intensity levels may be routed through one or more A/D converters 216 (step 231). The resulting digitized holographic data may then be organized for efficient retrieval and stored at the nonvolatile memory 218 (e.g., a hard disk) along with the velocity data and the recording time data recorded by the flight tracking system 229 (step 232). Either in parallel with data collection or at any time thereafter, the digitized holographic data may be integrated with the velocity information and the recording time information to obtain time-dependent particle distribution information associated with each recorded sample volume 224 (step 234). The time-dependent particle distribution information may then be transferred to the computer system 220 for processing (step 236). In other embodiments, the digitized holographic data, velocity information, and recording time information may be transferred separately to the computer 220, where it is integrated to form time-dependent particle distribution information.

Before reconstructing the holograms, estimates of the particle velocities are used to determine the effective pixel pitch of the M×N array 210 (where M<<N). The effective pixel pitch is then used to represent the X (time) axis as a spatial pixel pitch (step 237). Next, the computer processing system 220 may run the automatic reconstruction algorithms 221 discussed above to reconstruct holograms corresponding to each recorded sample volume $224_{1-n}$ (step 238) and determine three-dimensional position information (X-position, Y-position, Z-position) associated with the particles $226_{1-n}$ (step 240). Using the holograms and the three-dimensional position information, several particle properties may be measured, including, for example, size and spatial distributions of the properties $226_{1-n}$, number densities or particle concentrations of the particles $226_{1-n}$, and/or the shapes of the particles $226_{1-n}$ contained within the volume of interest 222 (step 242). Notably, the above steps may take place in any appropriate order. For instance, the digitized holographic data and the velocity and recording time information may be transferred to the processing computer 220 together or separately and in a single transfer or a series of transfers.

While various embodiments of the present invention have been described in detail, it is apparent that further modifications and adaptations of the invention will occur to those skilled in the art. For example, the systems and methods of particle measurement are generally described with respect to the measurement of aerosol particles (e.g., liquid and ice particles) within cloud volumes of interest that are measured using an airborne particle measurement instrument that is flown on an aircraft through the volume of interest. However, it should be understood that the systems and methods could be used with other methods of causing relative movement between the measurement instrument and the volume of interest. Further, it should be understood that the volume of interest need not be a cloud volume, but could be any particle-containing volume of interest. In this regard, the volume of interest may contain any type of particles within a flow. For example, the volume of interest may contain biological cells, bubbles, or chemically coated spheres within a flow. In essence, the utility may apply to analyze any type of particle-fluid flow having a mean velocity that is much higher than any variations in the mean velocity and that would benefit from a time-dependent analysis in the second dimension.

What is claimed:

1. A method of in situ particle measurement, comprising:
   moving a measurement instrument at a first velocity relative to a reference axis that intersects a volume of interest, wherein said volume of interest includes a number of particles to be measured, and wherein said particles are moving at a second velocity relative to said reference axis;
   transmitting, from said measurement instrument, a light beam across said volume of interest, wherein said light beam interacts with individual ones of said particles;
   using a sensor array of said measurement instrument, detecting incident light reflecting patterns associated with an interaction of said light beam with said particles; and
   using one or more computer processors:
   determining, based on said second velocity, an effective pixel pitch of said sensor array along said reference axis; and integrating data collected over time using said sensor array to form one or more holograms, wherein said holograms provide cumulative information regarding said particles of said volume of interest as a function of time along said reference axis.

2. The method of claim 1, wherein said integrating comprises reconstructing said holograms using an automated reconstruction algorithm running on said one or more computer processors.

3. The method of claim 2, wherein said automated reconstruction algorithm comprises a Rayleigh-Sommerfeld kernel.

4. The method of claim 1, further comprising determining three-dimensional position information for each said particle within said volume of interest, wherein said three-dimensional position information comprises an X-position, a Y-position, and a Z-position, and wherein said X-position is a position along said reference axis, and said Z-position is a position along an optical axis.

5. The method of claim 4, wherein said determining said X-position comprises correlating said second velocity to said data collected over time using said array.

6. The method of claim 1, wherein said second velocity fluctuates.

7. The method of claim 1, wherein said light beam is one of a laser sheet and a laser beam.

8. The method of claim 1, wherein said particles comprise one or more of ice particles and liquid particles.

9. The method of claim 1, wherein one or more of said particles are spherical, isometric, quasi-isometric, or irregular.

10. The method of claim 1, wherein said sensor array is a linear photodiode array.

11. The method of claim 10, wherein said photodiode array is a one-dimensional array having between 128 and 1024 pixels.

12. The method of claim 11, wherein each said pixel is one of a 3, 4, 5, 6, 7, or 8 bit pixel.

13. The method of claim 1, wherein said sensor array is arranged in rows of one of M×N pixels, wherein M<<N.

14. The method of claim 1, wherein said patterns associated with said interaction of said light beam with said particles are interference patterns.

15. The method of claim 14, wherein said interference patterns represent holographic electric fields.

16. The method of 1, further comprising storing said data collected over time using said array to a memory prior to said step of processing said data.

17. The method of claim 1, further comprising using said holograms to determine one or more of a size distribution of said particles, a spatial distribution of said particles, a number density of said particles, and a shape of one or more of said particles within said volume of interest.

18. A method of particle measurement, comprising:
receiving first input information regarding a rate of relative motion between a measurement instrument and numerous particles to be measured within a volume of interest, wherein said measurement instrument transmits a light beam across said volume of interest;
receiving, from a detector array, second input information relating to incident light scattering patterns associated with an interaction of a substantially unfocused portion of said light beam with individual ones of said particles; and
by operating one or more processors, using said first and second input information to obtain at least a statistically meaningful sampling of time-dependent particle distribution information for said volume of interest, wherein said time-dependent particle distribution information relates to at least one of a spatial distribution of said particles, a size distribution of said particles, a number density of said particles, and a shape of said particles within said volume of interest.

19. The method of claim 18, wherein said statistically meaningful sampling of said time-dependent particle distribution information encompasses all of said particles within an entirety of said volume of interest.

20. The method of claim 18, further comprising reconstructing one or more time-dependent holograms using said time-dependent particle distribution information, wherein said one or more time-dependent holograms are used to generate the size distribution of said particles.

21. The method of claim 20, wherein said reconstructing is accomplished via an automated reconstruction algorithm running on said one or more processors.

22. The method of claim 18, wherein said rate of relative motion between said measurement instrument and said volume of interest fluctuates.

23. The method of claim 18, wherein said particles comprise one or more of liquid particles and ice particles.

24. The method of claim 18, wherein one or more of said particles is between 1 μm and 200 μm in diameter.

25. The method of claim 18, wherein said light beam comprises substantially collimated light.

* * * * *